United States Patent [19]

Henderson et al.

[11] Patent Number: 5,145,975
[45] Date of Patent: Sep. 8, 1992

[54] NAPHTHOQUINONE DERIVATIVES

[75] Inventors: Graeme B. Henderson; Peter C. Ulrich, both of New York; Anthony Cerami, Shelter Island, all of N.Y.

[73] Assignee: The Rockefeller University, New York, N.Y.

[21] Appl. No.: 549,410

[22] Filed: Jul. 6, 1990

Related U.S. Application Data

[62] Division of Ser. No. 199,664, May 27, 1988, Pat. No. 4,942,170.

[51] Int. Cl.$^5$ .................. C07C 129/12; C07C 50/12
[52] U.S. Cl. .................. 552/299; 544/139; 544/146; 544/152; 544/370; 544/379; 546/210; 546/212; 546/214; 546/231; 548/342; 549/68; 549/76; 549/474; 549/493
[58] Field of Search .................. 552/299

[56] References Cited

PUBLICATIONS

Henderson et al., "Chemical Abstracts", vol. 109, 1988, Col. 109:162916z.
Jockers-Scheruebl et al., "Chemical Abstracts", vol. 110, 1989, Col. 110:131001p.
Henderson et al., "Chemical Abstracts", vol. 112, 1990, Col. 112:229719v.

*Primary Examiner*—Jane T. Fan
*Assistant Examiner*—James H. Turnipseed
*Attorney, Agent, or Firm*—Klauber & Jackson

[57] ABSTRACT

The present invention relates to the treatment of diseases caused by invading organisms in a host by first identifying an enzymatic difference between the host and the invading organism and then administering to the host a pharmaceutically effective amount of a subversive substrate for the differing enzyme of the invading organism, whereby the action of the differing enzyme causes a result counter to the intended result and function of the enzyme that results in its debilitation or death. In particular, treatment of parasitic diseases caused by kinetoplastids including trypanosomes and leishmanias, e.g., African sleeping sickness, Chagas' disease, oriental sore and kala-azar is accomplished by administration of a pharmaceutically effective antiparasitic amount of a competitive toxigenic substrate for trypanothione reductase. Methods of treatment and compositions therefor contain a competitive toxigenic substrate for trypanothione reductase. Numerous compounds and corresponding compositions are disclosed.

2 Claims, 4 Drawing Sheets

ENZYMATIC REDUCTION OF COMPOUNDS (A,B) AS A FUNCTION OF SUBSTRATE CONCENTRATION.

ENZYMATIC REDUCTION OF TEST COMPOUNDS AND PRIOR ART COMPOUNDS AS A FUNCTION OF SUBSTRATE CONCENTRATION. RELATIVE RATES WERE MEASURED UNDER AEROBIC CONDITIONS BY COUPLING SUPEROXIDE PRODUCTION TO CYTOCHROME C REDUCTION AS DESCRIBED.

INCUBATION OF COMPOUND E WITH TRYPANOTHIONE REDUCTASE UNDER AEROBIC (a) AND ANAEROBIC (b) CONDITIONS, AS DESCRIBED IN TEXT.

NAPHTHOQUINONE DERIVATIVES

This work was supported by a grant from the Rockefeller Foundation, grants from the National Institutes of Allergy and Infectious Diseases and a National Institutes of Health Postdoctoral Fellowship.

This is a division of application Ser. No. 07/199,664, file° May 27, 1988 now U.S. Pat. No. 4,942,170.

BACKGROUND OF THE INVENTION

There is great need for new and less toxic treatments for human tropical diseases caused by parasitic kinetoplastids including trypanosomes (African sleeping sickness and Chagas' disease (American trypanosomiasis)) and leishmanias (oriental sore and kala-azar). In the case of Chagas' disease which is caused by *Trypanosoma cruzi*, there is currently no generally effective chemotherapy for the millions of people infected.

Among parasitic diseases, *Trypanosoma cruzi* infection is particularly difficult to treat by chemotherapy. At present the only drugs which are clinically available to treat Chagas' disease are nitroaromatic derivatives, but the well-documented host toxicity associated with such compounds has severely limited their application. While it has been apparent for some years that the antiparasitic action of nitroaromatic drugs involves reduction of the nitro function by parasite enzymes, attempts to improve the therapeutic index of these compounds have proceeded slowly on an ad hoc basis as the parasite enzymes responsible for nitro-reduction have not been identified. It has been found that the unique kinetoplastid enzyme, trypanothione disulfide reductase, can catalyze redox-cycling activity.

All pathogenic species of Kinetoplastida which have been examined are found to possess trypanothione and the enzyme, trypanothione disulfide reductase, which maintains a high intracellular concentration of this compound in the reduced (dithiol) form. As trypanothione reductase is ubiquitously distributed in Kinetoplastida and has no direct mammalian counterpart, it therefore represents an extremely important target for chemotherapy. The mammalian equivalent of trypanothione reductase is the enzyme glutathione disulfide reductase. Previous attempts to interrupt the activity of enzymes of this class have been based up on alkylating or acylating agents, but such approaches have, so far, met with little practical success. A need therefore exists for a therapeutic protocol and corresponding pharmaceutically effective compositions which will exhibit the requisite specificity and safety to successfully subvert the purpose of the anti-oxidant enzyme trypanothione reductase.

SUMMARY OF THE INVENTION

In a first specific aspect, the present invention relates to a method of treating diseases caused by parasitic kinetoplastids, including trypanosomes and leishmanias, and compositions useful therefor. More particularly, the present invention concerns a method of treating parasitic kinetoplastids in a host vertebrate which comprises the administration of a pharmaceutically effective, antiparasitic amount of a competitive toxigenic substrate for trypanothione reductase.

Further to the above, the instant invention comprises therapeutic compositions adapted for administration to a host vertebrate infected with a parasitic kinetoplastid organism which contain a pharmaceutically effective antiparasitic amount of a competitive toxigenic substrate for trypanothione reductase.

The present invention is predicated on the broader discovery that a difference exists between the enzymatic profile of a host organism and an injury-promoting invading organism. It is accordingly proposed to identify a difference in the enzymatic profile between the host and the invader and to administer to the host bearing the invader a quantity of a substrate specific for the differing invader enzyme, that will compete with the conventional and intended substrate for that enzyme, and that by so doing, will cause the differing enzyme to pursue an activity that will at the least divert the enzyme from its intended function and preferably will cause the differing enzyme to act in contradiction to such function.

Accordingly, in its broadest aspect, the present invention relates to the treatment of an animal host afflicted with a disease caused at least in part by an invading organism by first identifying an enzymatic difference between the host and the invading organism and then administering to the host a pharmaceutically effective amount of a subversive substrate for the differing enzyme of the invading organism that subverts the action of the differing enzyme to cause a result counter to the intended result and function of the enzyme, and which promotes the debilitation or death of the invading organism. Likewise, therapeutic compositions containing a pharmaceutically effective amount of the subversive substrate are contemplated.

A further discovery of the present invention is that trypanothione reductase is capable of reducing compounds which in turn readily undergo auto-oxidation with concomitant production of superoxide. This ability of trypanothione reductase to catalyze reduction of compounds which spontaneously re-oxidize producing superoxide constitutes a reversal or subversion of the enzyme's normal physiological role. Thus, trypanothione reductase which is normally an integral part of the anti-oxidant defense process is induced by the compounds of this invention to become a source of oxidant stress. These compounds are therefore competitive toxigenic substrates or "subversive substrates" for trypanothione reductase; in the presence of $O_2$ they do not inactivate the enzyme but a) cause the production of free radicals, b) inhibit $T(S)_2$ reduction and c) cause futile consumption of NADPH. Such a combination of potentially cytotoxic events is highly detrimental within the environment of the kinetoplastid cell.

Accordingly, it is a principal object of the present invention to provide a method for inducing the mortality of invading organisms in a host by subverting the activity of one or more enzymes of the invader to promote the debilitation or death thereof.

It is a further object of the present invention to provide a method as aforesaid wherein said invading organisms are parasitic and the mortality of said parasitic organisms is induced in part by the development and maintenance of intolerable levels of oxidant stress.

It is a still further object of the present invention to provide a method as aforesaid wherein said intolerable levels of oxidant stress are in part caused by the subversion of the reducing activity of an enzyme normally found in said parasitic organism.

It is a still further object of the present invention to provide a method as aforesaid wherein the subversion of said enzyme is accompanied by the production of superoxide compounds that raise parasite organism oxidant stress.

It is a still further object of the present invention to provide a method as aforesaid wherein the subversion of said enzyme is also accompanied by the futile consumption of NADPH.

It is a still further object of the present invention to provide therapeutic compositions that may be administered to a host bearing said parasitic organisms to induce the mortality of said parasitic organisms as aforesaid.

Other objects and advantages will become apparent to those skilled in the art from a review of the ensuing description which proceeds with reference to the following illustrative drawings.

DETAILED DESCRIPTION OF THE INVENTION

Figure 1:
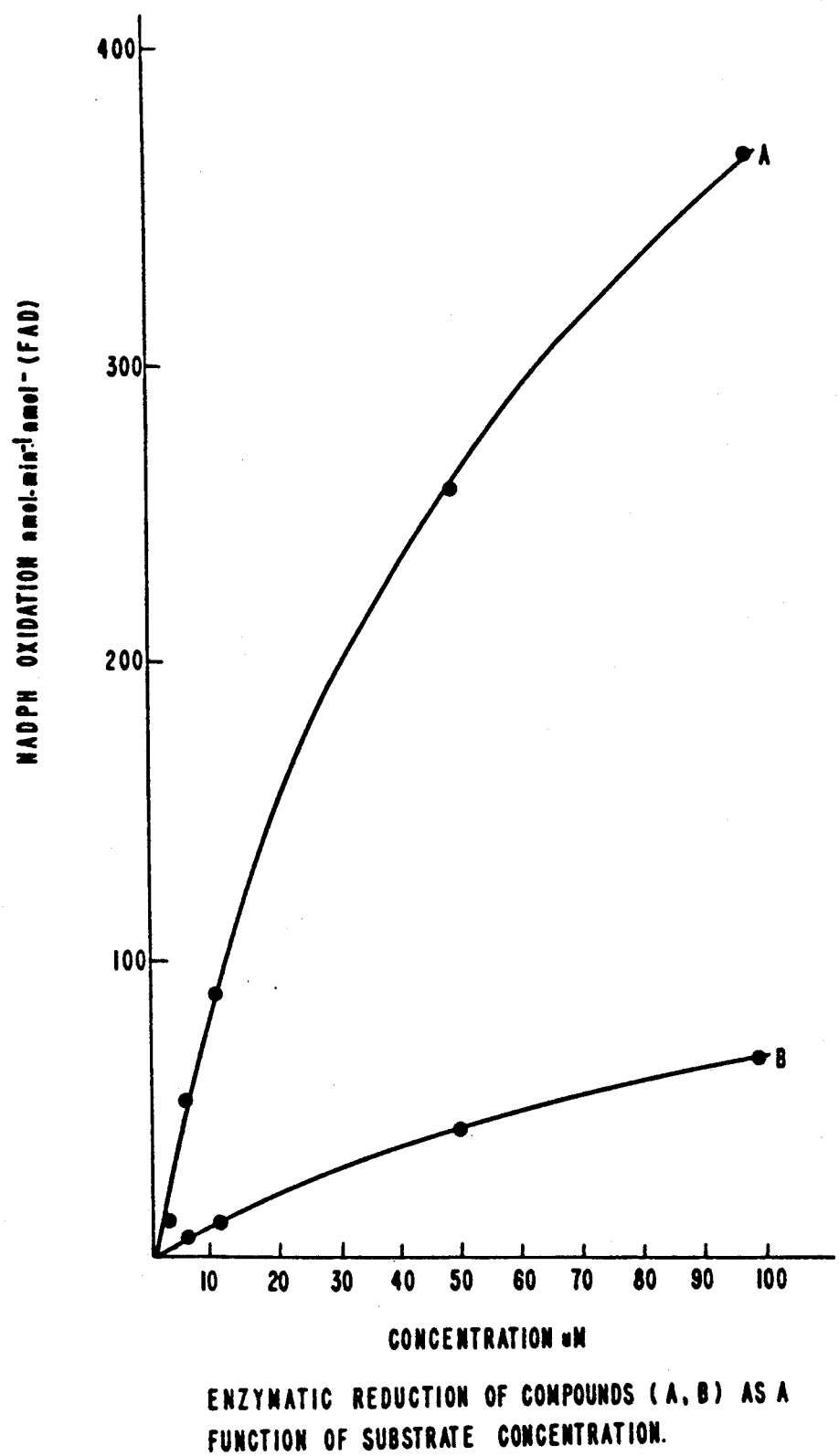
FIG. 1 is a graph of the results of the enzymatic reduction of compounds A and B of the present invention as a function of substrate concentration.

In its broadest aspect, the present invention relates to the treatment of disease caused by an invading organism in a host, by a method comprising comparing the enzyme profile of the host and the invading organism and identifying one or more differing enzymes in the invading organism that differ in structure or function from the enzymes of the host, and administering to the host a pharmaceutically effective amount of a subversive substrate for at least one of the differing enzymes, whereby the action of the differing enzymes causes a result opposite in purpose thereof and promotes the debilitation or death of the invading organism.

Thus, the present invention proposes to treat diseases caused by invading organisms in a host by first identifying an enzymatic difference between the host and the invading organism and then administering to the host a pharmaceutically effective amount of a substrate for the differing enzyme of the invading organism that subverts the action of the differing enzyme to cause a result counter to the intended result and function of the enzyme. This "subversive" substrate possesses certain of the structural attributes of the conventional substrate for the enzyme and thereby causes the enzyme to react with it, however, other structural characteristics are also present that cause the enzyme's action to promote a condition in the invading organism that disrupts rather than maintains homeostasis and that results in the debilitation or death of the invader.

As noted above, the present invention is predicated on the discovery that a difference exists between the enzymatic profile of a host organism and an injury-promoting invading organism. It is accordingly proposed to identify a difference in the enzymatic profile between the host and the invader and to administer to the host bearing the invader a quantity of a substrate specific for the differing invader enzyme, that will compete with the conventional and intended substrate for that enzyme, and that by so doing, will cause the differing enzyme to pursue an activity that will at the least divert the enzyme from its intended function and preferably will cause the differing enzyme to act in contradiction to such function. The principles of the invention are evident in the action and treatment of kinetoplastids, and the remainder of the description directs itself to this system by way of illustration, and not limitation.

Comparative studies on the metabolism of Kinetoplastida and their vertebrate hosts have pointed to a number of biochemical differences which can be exploited as targets for chemotherapy. Investigation of the biochemical basis for the sensitivity of parasitic protozoa towards reagents which promote free radical damage in cells has led to the discovery that kinetoplastids possess highly unusual anti-oxidant defense mechanisms which are based upon the glutathione-spermidine conjugate, $N^1,N^8$-bis(glutathionyl)spermidine, which has been given the trivial name trypanothione, see Fairlamb et al., Science, 227, 1485–1487 (1985) and Henderson et al., J. Chem. Soc., Chem. Comm., 593–594 (1986).

In most aerobic organisms, the tripeptide glutathione (GSH) and the glutathione reductase/glutathione peroxidase enzyme couple have key roles in the anti-oxidant defense process. By contrast, all species of Kinetoplastida examined to date lack classical glutathione reductase and glutathione-dependent peroxidase activities. Trypanosomatids possess instead a novel NADPH-dependent flavoprotein disulfide reductase (trypanothione reductase) which maintains trypanothione in the dithiol $(T(SH)_2)$ form within the cell. In addition, kinetoplastids also possess trypanothione-dependent peroxidase activity. Given that anti-oxidant defenses of kinetoplastids are based upon trypanothione, inhibition of trypanothione reductase or subversion of its anti-oxidant role within the cell is a method by which a drug can be used to treat kinetoplastid infections.

Trypanothione disulfide reductases have been purified from Crithidia fasciculata and Trypanosoma cruzi and found to have similar physical and chemical properties to human glutathione reductase. In fact, it appears that trypanothione and glutathione reductase reduce their respective physiological disulfide substrates by the same catalytic mechanism. The parasite and human enzymes do, however, differ in their respective substrate specificities; glutathione disulfide (GSSG) is neither a substrate nor an inhibitor of trypanothione reductase and conversely, trypanothione disulfide $(T(S)_2)$ is not a substrate for glutathione reductase. This mutually exclusive substrate specificity is of key importance in the selective inhibition of trypanothione reductase. In a study on the substrate specificity of trypanothione reductase, the enzyme was shown to reduce various analogues of $T(S)_2$ in which the spermidine moiety had been replaced by an aliphatic side chain which contained at least one amine function. The activity of the enzyme with these analogues most closely reflected the relative ability of the compounds to bind in the active site and suggested that trypanothione reductase might possess a binding site for the spermidine moiety of T(S)$_2$, Henderson et al., *Biochemistry*, 26, 3023-3027 (1987).

Having identified trypanothione reductase as a potential target for chemotherapeutic intervention, the instant invention presents compounds which effectively subvert the physiological function of this enzyme. These compounds take advantage of the ability of trypanothione reductase to catalyze reduction of substances which can undergo redox-cycling processes to produce toxic metabolites of oxygen which can cause parasite mortality and, for example, have been shown to kill *T. cruzi* trypomastigotes.

The present invention thus provides a method of treatment for diseases caused by the parasitic kinetoplastids in a host vertebrate which comprises administration to the host vertebrate of a pharmaceutically effective antiparasitic amount of a competitive toxigenic substrate for trypanothione reductase.

In general, the competitive toxigenic substrate described herein has been constructed to share three inherent properties; first, specific moieties have been included to mimic the alkyl-substituted amine functions of the spermidine portion of trypanothione itself; these basic groups confer binding affinity for trypanothione reductase. Second, specific redox-active aromatic systems have been incorporated which are capable of undergoing one- or two-electron reductions by the active site of trypanothione reductase. Third, these redox-active systems are of a type such that, under aerobic conditions and after reduction by the enzyme, the reduced system is capable of reducing oxygen to form active oxygen species such as superoxide and hydrogen peroxide, which are toxic to the parasite.

More particularly, the competitive toxigenic substrate for trypanothione reductase is a compound selected from the group consisting of compounds of the structural formula, $$R^1C(X)=NNHC(=Z)NHR^2 \qquad (I)$$

wherein,
$R^1$ = H, or lower alkyl
X = reducible aromatic system, or reducible arylalkyl group
Z = O, S, or NH
$R^2$ = H, or an alkylaminoalkyl group of the formula:

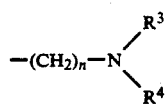

wherein n is an integer of from 1 to 6 and $R^3$ and $R^4$ are each independently a lower alkyl group or together form a part of a cycloalkyl or heterocyclic ring containing from 1 to 2 heteroatoms, of which at least one is nitrogen; and the second of said heteroatoms is selected from the group consisting of nitrogen, oxygen, and sulfur; with the proviso that when the second of said heteroatoms of the heterocyclic ring is nitrogen and forms a piperazine ring, it may be optionally substituted by a substituent that is identical to the portion of the compound on the first nitrogen of the piperazine ring. Alternatively, when $R^3$ is lower alkyl, $R^4$ may be a second group of structure $R^1C(X)=NNHC(=Z)NH(CH_2)_n$—, with $R^1$, X, Z and n having values as defined hereinabove and said second group of $R^4$ being identical to such group already attached to the nitrogen which bears the first group of $R^4$.

The ring system of X may be selected from numerous quinoid and homocyclic or heterocyclic variants, such as the naphthoquinone, nitrofuranyl, nitrothienyl, and nitroimidazolyl ring systems, or other analogous systems, which are capable of reduction by the active site of trypanothione reductase.

The lower alkyl groups referred to above contain one to six carbon atoms and may be methyl, ethyl, propyl, butyl, pentyl, or hexyl and their corresponding branched-chain isomers.

The heterocyclic ring formed by nitrogen and the $R^3$ and $R^4$ group can be any of the well-known substituted or unsubstituted heterocyclic rings such as piperidinyl, piperazinyl, morpholinyl, or pyrrolidinyl.

Particularly preferred compounds of formula I are those structures wherein X is 2-(1,4-naphthoquinon-2-yl)ethyl, e.g.,

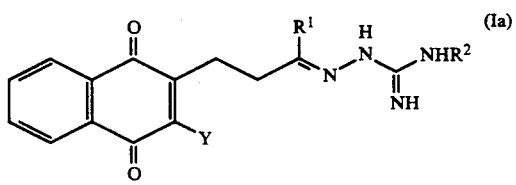

wherein $R^1$ and $R^2$ are as hereinbefore defined and Y is a hydrogen, a methyl group, or a group of the formula

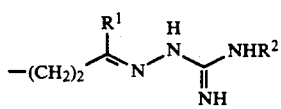

wherein $R^1$ and $R^2$ are as hereinbefore defined; or those compounds of formula I wherein X is a 5-nitrofuranyl group, e.g.,

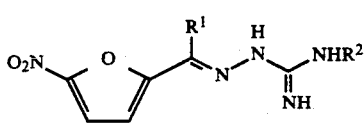

wherein $R^1$ and $R^2$ are as hereinbefore defined.

The compounds of formulae Ia and Ib are preferred compounds due to their highly effective competition as toxigenic substrates for the trypanothione reductase enzyme. By virtue of this competitive toxigenic substrate role, the compounds exhibit their antiparasitic effects which make them highly desirable for the treatment of the parasitic infections by kinetoplastids including trypanosomes and leishmanias.

Certain of the compounds of formula Ib are known; e.g., the compound wherein $R^1$ and $R^2$ are both hydrogen, and Z is NH, is known as guanofuracin.

Other compounds of formulae Ia and Ib are preparable by known standard chemical reactions. The requisite precursors for compounds of formula Ia are, for instance, prepared by reaction

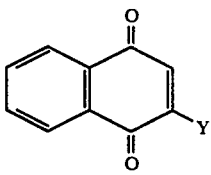

wherein Y is methyl or hydrogen with a 4-oxoalkanoic acid and silver nitrate in an aqueous polar solvent such as acetonitrile, followed by treatment with ammonium peroxydisulfate to afford intermediates of the formula

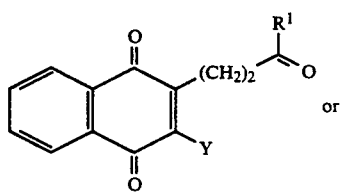

or

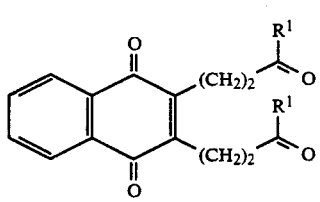
(II)

wherein $R^1$ is as hereinbefore described.

The compounds of formula Ia and Ib are then prepared by reacting a compound of formula II, or a 5-nitro-2-acylfuran of formula III,

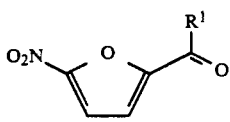
(III)

respectively, with hydrazinecarboximidamide or with appropriate N-substituted hydrazinecarboximidamides of formula

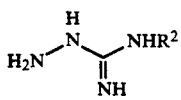

wherein $R^2$ is hereinbefore described, or their acid addition salts, in a polar solvent at reflux temperatures for a period of one-half to 48 hours. Suitable solvents are those such as methanol and ethanol, and the reflux temperature is, of course, dependent upon the particular solvent chosen. N-substituted hydrazinecarboximidamides are readily available by reaction of hydrazinecarboximidothioic acid ethyl ester with amines or by other methods known to those skilled in the art.

The various compounds of the present invention can be utilized in either their base form or as their corresponding pharmaceutically acceptable acid addition salts or products. Such acid addition salts can be derived from a variety of organic and inorganic acids such as sulfuric, phosphoric, hydrochloric, hydrobromic, hydroiodic, sulfamic, citric, lactic, maleic, malic, succinic, tartaric, cinnamic, acetic, benzoic, gluconic, ascorbic, and related acids.

The compounds of the present invention can be utilized in the method of the present invention in a variety of commonly utilized pharmaceutical formulations comprising the aforementioned compounds in admixture with a pharmaceutical carrier.

The dosage administered of the compounds of the present invention is dependent upon the age and weight of the vertebrate being treated, the mode of administration, and the type and severity of the parasitic infection being prevented or treated. Typically, the dosage administered will be in the range of 1–500 mg per dosage unit.

For oral administration, the compounds may be formulated into compositions in the form of tablets, capsules, elixirs, or the like. For parenteral administration they may be formulated into compositions which are solutions or suspensions for intramuscular injection.

The following methods are utilized to ascertain the relative activity of the compounds of the present invention.

Enzyme Assays and Kinetic analysis

Trypanothione disulfide reductase activity is assayed spectrophotometrically by monitoring substrate-dependent oxidation of NADPH at 340 nm. Alternatively, enzyme activity is monitored by coupling radical formation to cytochrome C reduction and measuring absorbance changes ($\epsilon_{550}=21$ mM$^{-1}$). Absorbance changes are monitored on a spectrophotometer with a thermostated cuvette chamber. Enzyme concentration is measured spectrophotometrically using the extinction coefficient ($\epsilon_{464}=11.3$ mM$^{-1}$, Shames et al., *Biochemistry*, 25, 3519–3526 (1986). Kinetic runs are carried out at 27° C. in 0.1 M 4-(2-hydroxyethyl)-1-piperazineethane sulfonic acid (HEPES) buffer, pH 7.8, containing 0.1 mM EDTA and 0.25 mM NADPH. Anaerobic measurements are performed in rubber stoppered cuvettes that have been flushed repeatedly with helium. All buffers and solutions used in the assays are treated in this manner. Additions to the cuvette are made with a microsyringe piercing the septum.

Interaction of Trypanothione Reductase with Compound E under Aerobic and Anaerobic Conditions Assays are carried out in 0.1 M HEPES, pH 7.8, containing 1 mM EDTA, 0.15 mM NADH, 500 pmoles/ml trypanothione reductase and 10 μM nitrofuran VIII. Reactions are started by addition of enzyme (80 μl to a 2 ml assay). Sequential spectra (200–800 nm) are collected at 20 sec intervals using a UV/Vis spectrophotometer. At the end of the experiment, the assay mixtures are dialyzed and trypanothione reductase is assayed using 250 μM T(S)$_2$.

Parasite Cell Culture

Human saphenous vein smooth muscle (HSVSM) cells are isolated from outgrowths of explants of unused portions of veins harvested for coronary artery bypass surgery as described previously by Warner et al., *J. Exp. Med.*, 165, 1316–1331 (1987). The cells are maintained in DME medium containing 5.5 mM glucose, 25 mM HEPES and 10% FBS (Hy-Clone Laboratories, Logan, UT). *Trypanosoma cruzi* Strain Y trypomastigotes are propagated as described previously by Libby et al., *J. Clin. Invest.*, 77, 127–135 (1986), except that HSVSM cells are used in place of bovine aortic smooth muscle cells.

Trypanocidal Assays

Test compounds are dissolved in 0.3 ml DMSO and brought to volume by dilution with serum-free DME medium. Solutions are sterilized by filtration through 0.22 μm filter units. Trypomastigotes ($10^7$ ml$^{-1}$) are harvested and washed twice in serum-free DME medium. Parasites are added to solutions of the test compounds to a final concentration of $10^6$ ml$^{-1}$ and incubated for 3 hours at 37° C. in a 5% $CO_2$ atmosphere. After incubation with the test compound, 0.1 ml of the parasite suspension ($10^5$ organisms) is diluted with 0.4 ml cell culture medium and added to a culture of HSVSM cells. After 16 hours, the HSVSM cells are washed to remove non-internalized trypomastigotes and resupplied with fresh culture medium. Infections are followed for 4–7 days by light microscopy.

When the compounds of the invention are tested as substrates for trypanothione reductase from *C. fasciculata*, oxidation of NADPH is readily measured. See FIG. 1 in this fully aerobic system. Certain of the compounds of the invention are found to oxidize several molar equivalents of NADPH, which suggests that redoxcycling is taking place. The substrates must undergo enzymecatalyzed reduction and subsequent reoxidation by $O_2$ with concomitant production of superoxide. This is confirmed by monitoring oxygen consumption directly (which was approximately stoichiometric with NADPH consumption) and by monitoring cytochrome C reduction by superoxide in the coupled assay system described above.

Figure 2:
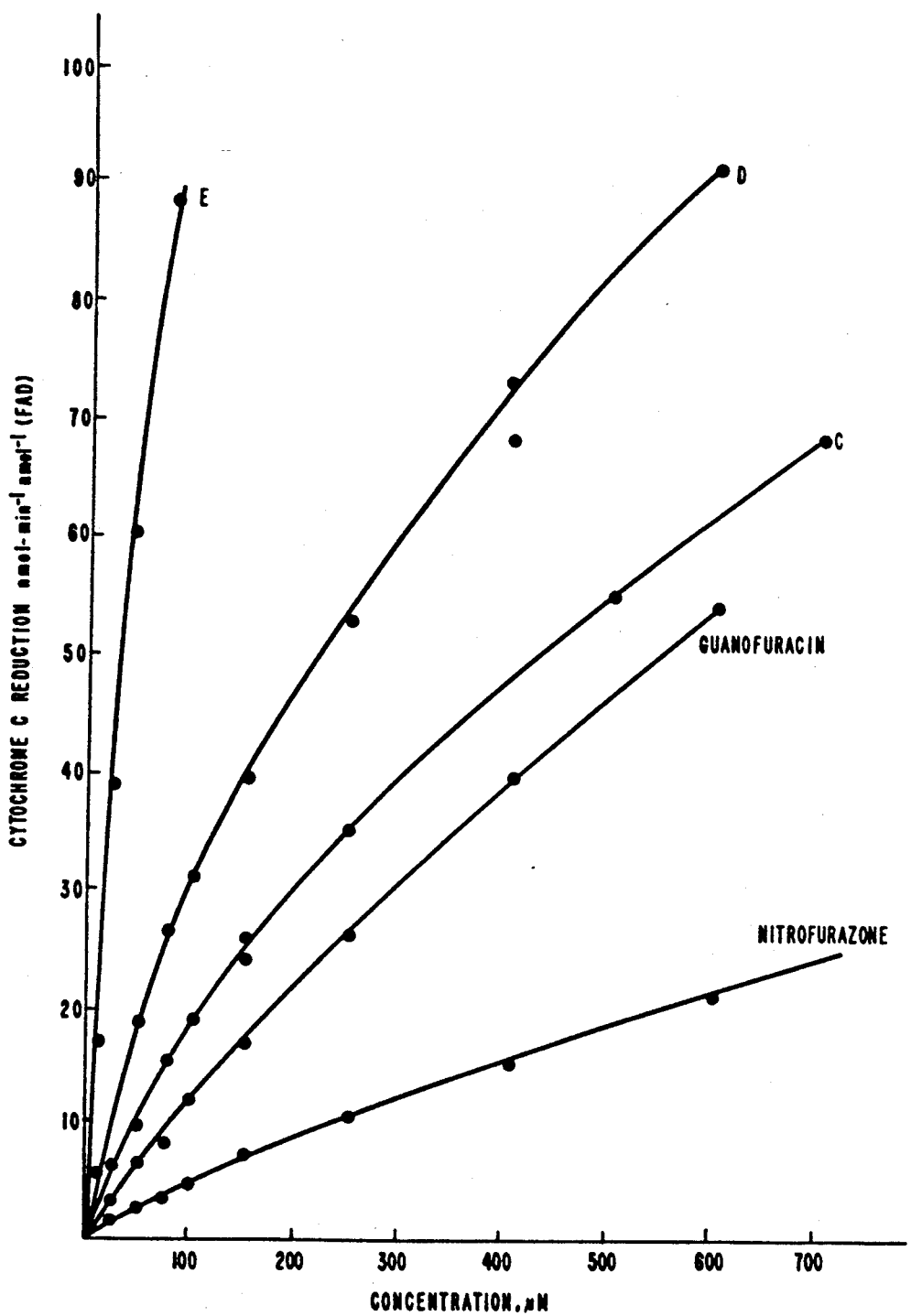
FIG. 2 is a graph of the results of the enzymatic reduction of compounds C, D and E of the present invention and comparative prior art compounds as a function of substrate concentration. Relative rates were measured under aerobic conditions by coupling superoxide production to cytochrome C reduction as described.

The ability of the compounds of this invention to undergo such a redox-cycling process is reflected by their low 1-electron reduction potential. Testing of the ability of trypanothione reductase to reduce two nitrofuran derivatives, nifurtimox and nitrofurazone, which have been used to treat trypanosomatid infections, reveals trypanothione reductase-catalyzed reduction of these compounds that could be detected by monitoring NADPH oxidation. Redox-cycling is evident by coupling superoxide production to cytochrome C reduction (FIG. 2). When certain of the compounds of the present invention are tested as substrates for trypanothione reductase (FIG. 2), they are found to be considerably more reactive than either nitrofurazone or nifurtimox (nifurtimox not shown on the figure).

Figure 3:
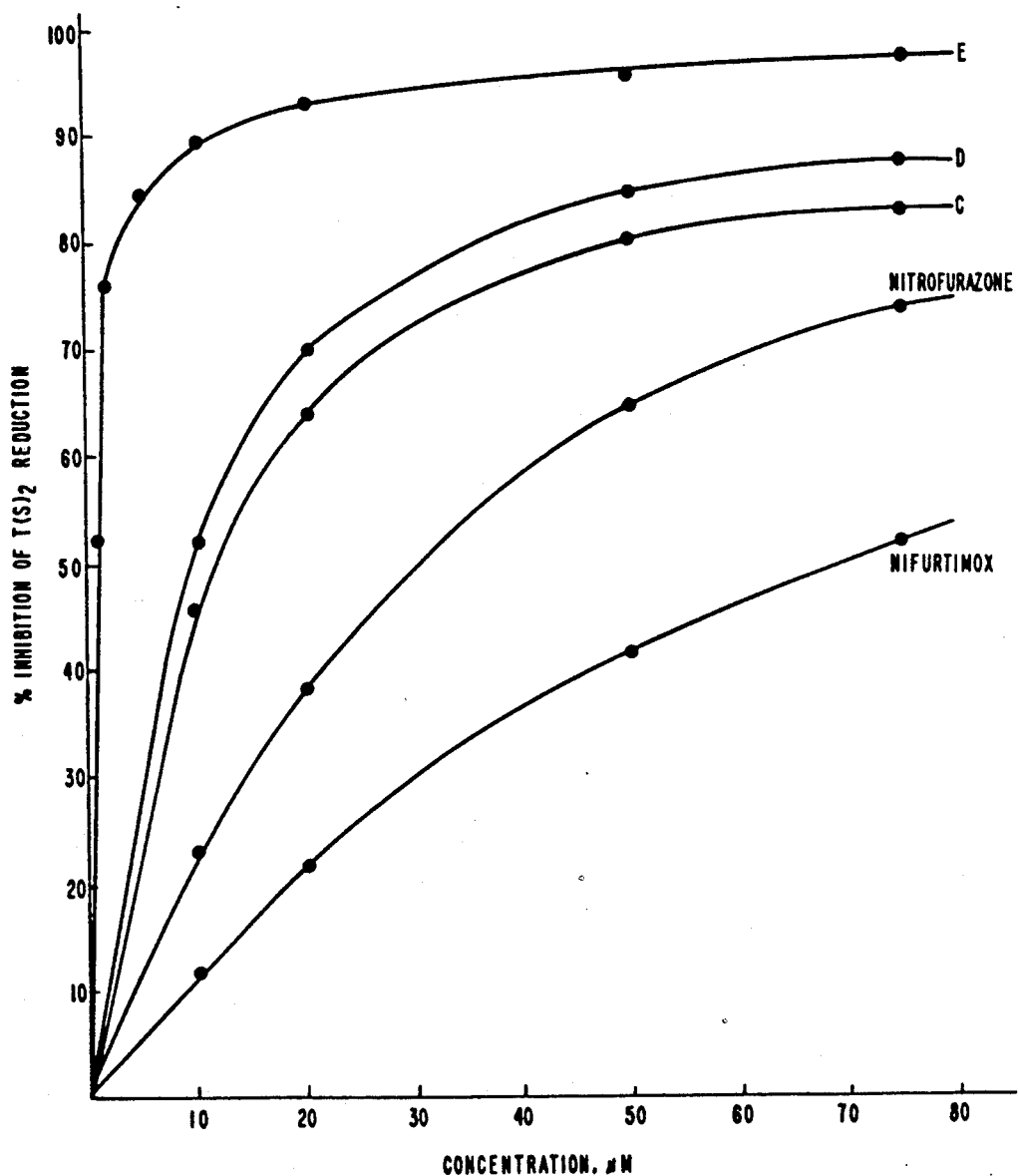
FIG. 3 is a graph of the results of tests of the inhibition of $T(S)_2$ reduction by compounds C, D and E of the present invention and comparative prior art compounds under aerobic conditions. $T(S)_2$ concentration was 250 $\mu$M; enzyme, 0.3 U/ml; NADPH, 150 $\mu$M.

The compounds of the invention also possess the ability to inhibit trypanothione reductase-catalyzed $T(S)_2$ reduction as illustrated by the data presented in FIG. 3. The effect of the test compounds on this process correlates exactly with the relative ability of the compounds to undergo enzyme-catalyzed reduction; the most active substrates being also the best inhibitors of $T(S)_2$ reduction. The inhibition of trypanothione reductase-catalyzed $T(S)_2$ reduction is reversed following removal of the test compound by dialysis.

Figure 4:
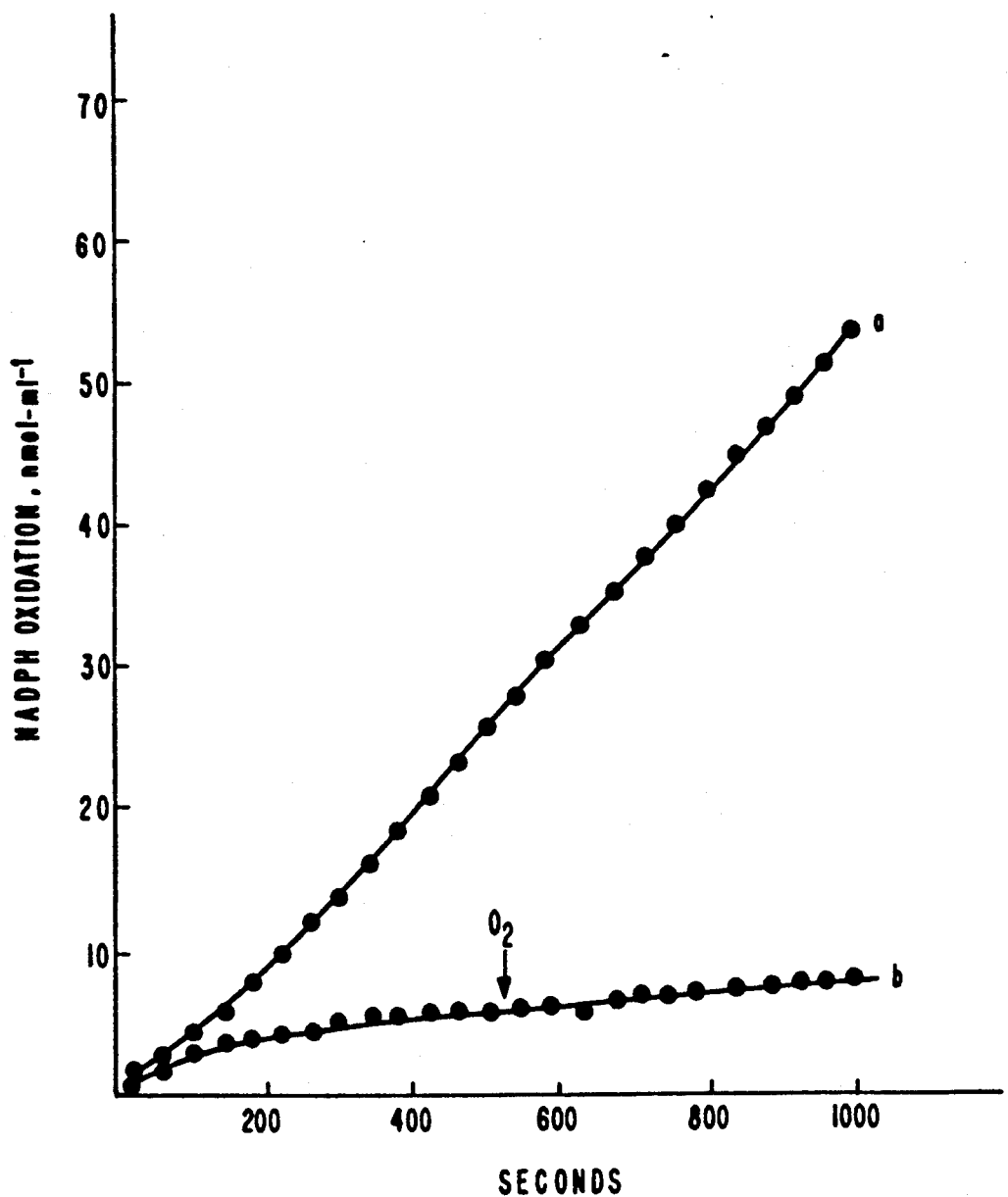
FIG. 4 is a graph of the results of the incubation of Compound E with trypanothione reductase under aerobic (a) and anaerobic (b) conditions, as described later on herein.

The foregoing experiments are carried out in the presence of saturating $O_2$; under anaerobic conditions, the interaction of the test compounds with trypanothione reductase was found to take a quite different course. For instance, when trypanothione reductase is incubated with the bis-nitrofuran derivative (compound E) in the presence or absence of $O_2$, the results are shown in FIG. 4. Under aerobic conditions, NADPH oxidation is linear with time (trace A). Under anaerobic conditions (trace B), the rate of NADPH oxidation is non-linear after an initial period and does not increase upon subsequent addition of $O_2$. At the end of the incubation (t=1000 sec), the assay mixtures A and B are dialyzed extensively to remove the substrate and then assayed for $T(S)_2$ reductase activity. The enzyme which had been incubated in the absence of $O_2$ is found to have lost 93% $T(S)_2$ reductase activity relative to the aerobic control and is no longer active with the test compounds.

Pretreatment of cultured *T. cruzi* trypomastigotes with the reactive naphthoquinone and nitrofuran trypanothione reductase substrates markedly decreases the capacity of the parasite to infect human smooth muscle cells as shown in Table 1, below.

TABLE 1

| Compound | Concentration, μM | | | |
|---|---|---|---|---|
| | 10 | 5 | 1 | 0.5 |
| Nifurtimox | 4 | 10 | 100 | 100 |
| Compound B | 8 | 21 | 100 | 100 |
| Compound A | 0 | 0 | 0 | 14 |
| Guanofuracin | 0 | 0 | 45 | 100 |
| Compound D | 0 | 0 | 35 | 64 |
| Compound E | 0 | 0 | 0 | 100 |

Trypomastigotes were pre-incubated with a test compound or a prior art compound as described above. Results are expressed as the percentage of cells infected by pre-treated trypomastigotes relative to untreated controls.

The effects of the compounds of the present invention have also been tested in an ongoing infection model. Human smooth muscle cells are infected with trypomastigotes and after 16 hours all parasites which did not infect are removed by washing. The cells are then incubated for 48 hours after which time the test compounds are added to the cultures and incubated for 16 hours After 16 hours, the treated culture media is replaced with drugfree fresh media and cell culture is continued for a further 24 hours. Levels of parasitemia in the treated and untreated cultures are then examined. The results are given below in Table 2.

TABLE 2

| Compound | Concentration μM | Trypomastigotes/ml* |
|---|---|---|
| None | — | $1.85 \times 10^7$ |
| Compound A: | 10 | $1.35 \times 10^7$ |
| 2,3-bis(3-(2-amidinohydrazono)-butyl)-1,4-naphthoquinone dihydrochloride | 1 | $4.10 \times 10^7$ |
| Compound D: | 10 | $<2.00 \times 10^4$ |
| 2-(5-nitro-2-furanylmethylidene)-N-[3-(4-methylpiperazin-1-yl)-propyl]hydrazinecarboximidamide trihydrobromide | 1 | $1.80 \times 10^7$ |
| Compound E: | 10 | $2.85 \times 10^7$ |
| 2-(5-nitro-2-furanylmethylidene)-N,N'-[1,4-piperazinediylbis(3,1-propanediyl)]bishydrazine-carboximidamide tetrahydrobromide | 1 | $1.85 \times 10^7$ |

*Number of trypomastigotes/ml counted swimming above the HSVM cell monolayer 5 days after initial infection.

All reagents and chemicals are of the highest grade commercially available. Trypanothione disulfide $(T(S)_2)$ is chemically synthesized as described in Henderson et al., *J. Chem. Soc., Chem. Comm.* 593–594 (1988). Trypanothione disulfide reductase was purified from *C. fasciculata* as described in Shames et al., *Biochemistry.* 25, 3519–3526 (1986).

The following examples describe in detail the procedures for the preparation of compounds utilizable in the present invention. It will be apparent to those skilled in the art that many modifications, both of materials and methods, can be practiced without departing from the spirit and scope of this invention.

EXAMPLE 1

2,3-Bis(3-(2-amidinohydrazono)butyl)-1,4-naphthoquinone dihydrochloride (Compound A)

Naphthoquinone (3.12 g, 20 mmol), 4-oxopentanoic acid (13.9 g, 120 mmol) and silver nitrate (2.0 g, 11.8 mmole) are combined in 30% aqueous acetonitrile at 65° C. A solution of ammonium peroxydisulfate (12.0 g, 52.6 mmole) is added dropwise over 30 minutes while the stirred mixture is maintained at 65°–75° C. On cooling, the mixture is extracted with diethyl ether (300 ml). The extract is then washed with water (3×50 ml), 5% NaHCO$_3$ (2×50 ml) and brine (50 ml) and dried over MgSO$_4$. After filtration through active carbon, the ether solution is evaporated to give crude 2,3-bis(3-oxobutyl)-1,4-naphthoquinone which is recrystallized from aqueous ethanol to give 1.45 g product, mp 110°–112° C. This 2,3-bis(3-oxobutyl)-1,4-naphthoquinone (0.456 g, 1.53 mmole), aminoguanidine hydrochloride (0.46 g, 4.3 mmole) and a drop of concentrated HCl are combined in 5 ml of 90% ethanol and heated at reflux for 3 hours. On cooling, 2,3-bis(3-(2-amidinohydrazono)butyl)-1,4-naphthoquinone crystallizes from the reaction mixture, and recrystallization from ethanol gives 400 mg product, mp 181°–183° C.

EXAMPLE 2

2-Methyl-3-(2-amidinohydrazono)butyl-1,4-naphthoquinone hydrochloride (Compound B))

2-Methyl-3-(2-amidinohydrazono)butyl-1,4-naphthoquinone hydrochloride, mp 108°–110° C. is prepared in a manner similar to that of Example 1 by reaction of aminoguanidine hydrochloride with 2-methyl-3-(3-oxobutyl)-1,4-naphthoquinone. This naphthoquinone is prepared by reaction of 2-methyl-1,4-naphthoquinone, 4-oxopentanoic acid, silver nitrate and ammonium peroxydisulfide in a manner similar to that described above.

EXAMPLE 3

2-(5-Nitro-2-furanylmethylidene)-N-(3-dimethylaminopropyl) hydrazinecarboximidamide dihydrobromide (Compound C)

a. Hydrazinecarboximidothioic acid ethyl ester hydrobromide (10.0 g, 50 mmole) and 3-dimethylaminopropylamine (5.36 g, 52.5 mmole) are dissolved in ethanol (20 ml). The resulting mixture is stirred at room temperature for 18 hours and is then heated at reflux for 1 hour. On cooling, the mixture is diluted with isopropanol (20 ml) and 48% hydrobromic acid (5.6 ml) is added. On storage at −20° C., N-(3-dimethylaminopropyl)hydrazinecarboximidamide dihydrobromide, mp 82°–84° C., crystallizes from the reaction mixture.

b. 5-Nitro-2-furaldehyde (0.564 g, 4 mmole) and N-(3-dimethylaminopropyl)hydrazinecarboximidamide dihydrobromide (1.6 g, 5 mmole) are heated at reflux in 8 ml 95% ethanol for 1 hour. The title compound precipitates from solution on cooling and is recrystallized from ethanol, mp 131°–133° C.

EXAMPLE 4

2-(5-Nitro-2-furanylmethylidene)-N-[3-(4-methylpiperazin 1-yl)propyl]hydrazinecarboximidamide trihydrobromide (Compound D)

a. Following the procedure of paragraph a. of Example 3 using the appropriate starting materials, N-[3-(4-methylpiperazin-1-yl)propyl]hydrazinecarboximidamide trihydrobromide, mp 212° C. is produced.

b. Using the product of paragraph a. of this example and 5-nitro-2-furaldehyde in the procedure of paragraph b. of Example 3 affords the title compound, mp 217°–220° C. (dec.).

EXAMPLE 5

2,2′-Bis(5-nitro-2-furanylmethylidene)-N,N′-[1,4-piperazinediylbis(3,1-propanediyl)]-bishydrazinecarboximidamide tetrahydrobromide (Compound E)

a. Utilizing the appropriate starting materials and the procedure of paragraph a. of Example 3, N,N′-[1,4piperazinediylbis(3,1-propanediyl)]bishydrazinecarboximidamide tetrahydrobromide, mp 241°–244° C., is produced.

b. Following the procedure of paragraph b. of Example 3 utilizing the compound of paragraph a. of this example and 5-nitro-2-furaldehyde affords the title compound, mp 270°–275° C. (dec.).

EXAMPLE 6

2-(5-Nitro-2-furanylmethylidene)-N-(3-dimethylaminopropyl)-hydrazinecarboxamide hydrochloride (Compound F).

Acetone semicarbazone (23 g) and 3-dimethylaminopropylamine (24.5 g) were heated to 175° C. over 40 minutes, then cooled and partitioned between t-butyl methyl ether and brine. The ether layer was concentrated to give 13.2 g waxy solid 2-isopropylidene-N-(3-dimethylaminopropyl)hydrazinecarboxamide (mp 49°–53° C.). Of this, 2.0 g was boiled 8 hr. in water maintained at a volume of 20 ml, then treated with 1.67 ml 12N HCl and concentrated in vacuo to give 2.5 g crude N-(3-dimethylaminopropyl)hydrazinecarboxamide dihydrochloride as a syrup. One fifth of the latter was reacted with 5-nitro-2-furaldehyde (0.282 g) in 6 ml 1:1 methanol-ethanol containing 0.16 ml pyridine at reflux for 30 minutes. The mixture was cooled and treated with 10 ml isopropanol to give 0.51 g of the title compound as a yellow solid, mp 200°–202° C. (dec.).

EXAMPLE 7

2,2′Bis(5-nitro-2-furanylmethylidene)-N,N′-[methyliminobis(3,1-propanediyl)]bishydrazinecarboxamide hydrochloride (Compound G)

In a similar manner to the preceding example, acetone semicarbazone (23 g) was heated with 3,3′-(methyliminobis)propylamine to give 18.23 g 2,2′-bis(2-propylidene)-N,N′-[methyliminobis(3,1-propanediyl)-]bishydrazinecarboxamide (mp 113°–114° C), 3.415 g of which was boiled in water 12 hr., treated with 2.5 ml 12N HCl, and concentrated to give N,N′-[methyliminobis(3,1-propanediyl)]bishydrazinecarboxamide trihydrochloride as a syrup, one fifth of which was then reacted with 5-nitro-2-furaldehyde (0.564 g) in 5 ml methanol containing 0.325 ml pyridine at reflux for 30 minutes followed by addition of 10 ml isopropanol to give 0.776 g of the title compound, mp 158°–160° C.

EXAMPLE 8

2-(5-Nitro-2-furanylmethylidene)-N-(3-dimethylaminopropyl)hydrazinecarbothioamide methanesulfonate (Compound H)

N-(3-dimethylaminopropyl)hydrazinecarbothioamide (0.12 g) was reacted with 5-nitro-2-furaldehyde (0.15 g) in 5 ml ethanol at reflux for 15 minutes. The mixture was cooled and treated with methanesulfonic acid (0.055 ml) and isopropanol and stored at 4° C. to give 0.15 g of the title compound as orange needles, mp 184°–187° C.

EXAMPLE 9

Tablet Formulation

| | mg per tablet |
|---|---|
| 2-(5-Nitro-2-furanylmethylidene)-N,N'-[1,4 piperazinediylbis(3,1-propanediyl)]bishydrazine-carboximidamide tetrahydrobromide | 10 |
| Lactose, direct compression grade | 213 |
| Microcrystalline cellulose | 30 |
| Sodium lauryl sulfate | 20 |
| Cornstarch | 25 |
| Magnesium stearate | 2 |
| | 300 |

Mix together the stated active ingredient, lactose, microcrystalline cellulose, sodium lauryl sulfate and cornstarch. Pass through a No. 40 screen. Add the magnesium stearate, mix and compress into desired shape on a tablet machine.

EXAMPLE 10

Capsule Formulation

| | mg per tablet |
|---|---|
| 2,3-Bis(3-(2-amidinohydrazono)butyl)-1,4-naphthoquinone dihydrochloride | 10 |
| Lactose, U.S.P. | 213 |
| Microcrystalline cellulose | 30 |
| Sodium lauryl sulfate | 20 |
| Cornstarch | 25 |
| Magnesium stearate | 2 |

EXAMPLE 10-continued

Capsule Formulation

| | mg per tablet |
|---|---|
| | 300 |

Mix together the stated active ingredient, lactose, microcrystalline cellulose, sodium lauryl sulfate and cornstarch. Pass through a No. 80 screen. Add the magnesium stearate, mix and encapsulate into the proper two-piece gelatin capsule.

It is noted herein that Compounds D and E may be prepared using as starting materials certain novel compounds that are the subject of prior filed application Ser. No. 119,958, filed Nov. 13, 1987, now U.S. Pat. No. 4,908,446 commonly assigned. Specifically, N-[3-(4-methylpiperidin-1-yl)propyl]hydrazinecarboximidamide trihydrobromide served as the starting material for Compound D, while N,N'-[1,4-piperazinediyl-bis(3,1-propanediyl)]bishydrazinecarboximidamide tetrahydrobromide served as the starting material for Compound E. The synthesis of these starting materials is disclosed in the aforementioned Ser. No. 119,958, and to that extent the disclosure thereof is incorporated herein by reference.

It is further noted that Compound C may be prepared from the compound N-(3-dimethylaminopropyl)hydrazinecarboximidamide dihydrobromide, which latter compound is disclosed in U.S. Pat. No. 4,544,759. The text of this patent is likewise incorporated herein by reference to the extent of the disclosure therein of the preparation of the compound in question.

This invention may be embodied in other forms or carried out in other ways without departing from the spirit or essential characteristics thereof. the present disclosure is, therefore, to be considered as in all respects illustrative and not restrictive, the scope of the invention being indicated by the appended Claims, and all changes which come within the meaning and range of equivalency are intended to be embraced therein.

What is claimed is:

1. The compound which is 2,3-bis(3-(2-amidinohydrazono)-butyl)-1,4-naphthoquinone dihydrochloride.

2. The compound which is 2-methyl-3-(2-amidinohydrazono)butyl-1,4-naphthoquinone hydrochloride.

* * * * *